United States Patent
Sato et al.

(10) Patent No.: US 8,708,911 B2
(45) Date of Patent: Apr. 29, 2014

(54) ULTRASONIC IMAGING APPARATUS AND A METHOD FOR DISPLAYING DIAGNOSTIC IMAGES

(75) Inventors: Takeshi Sato, Nasushiobara (JP); Ryota Osumi, Nasushiobara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 494 days.

(21) Appl. No.: 11/937,063

(22) Filed: Nov. 8, 2007

(65) Prior Publication Data
US 2008/0161690 A1    Jul. 3, 2008

(30) Foreign Application Priority Data
Dec. 27, 2006   (JP) .................. 2006-351833

(51) Int. Cl.
*A61B 8/00*   (2006.01)

(52) U.S. Cl.
USPC ........................................... 600/441

(58) Field of Classification Search
USPC ........................ 600/407, 437–472
See application file for complete search history.

(56) References Cited

U.S. PATENT DOCUMENTS

| | | | | |
|---|---|---|---|---|
| 5,429,137 A | * | 7/1995 | Phelps et al. ........... | 600/455 |
| 5,720,291 A | * | 2/1998 | Schwartz ............... | 600/456 |
| 5,860,924 A | * | 1/1999 | Quistgaard ............. | 600/441 |
| 6,679,843 B2 | * | 1/2004 | Ma et al. ................. | 600/441 |
| 7,037,263 B2 | | 5/2006 | Sumanaweera et al. | |
| 7,119,810 B2 | * | 10/2006 | Sumanaweera et al. | 345/506 |
| 7,744,538 B2 | * | 6/2010 | Sumanaweera et al. | 600/455 |
| 8,021,300 B2 | * | 9/2011 | Ma et al. ................. | 600/437 |
| 2004/0138560 A1 | * | 7/2004 | Paladini ................. | 600/437 |
| 2005/0122333 A1 | | 6/2005 | Sumanaweera et al. | |

FOREIGN PATENT DOCUMENTS

| | | |
|---|---|---|
| JP | 10-165402 | 6/1998 |
| JP | 11-9603 | 1/1999 |
| JP | 2008-522272 | 6/2008 |
| WO | WO 2006/056741 A1 | 6/2006 |

OTHER PUBLICATIONS

Japanese Office Action issued Nov. 22, 2011, in Patent Application No. 2006-351833 (with partial English-language translation).

* cited by examiner

*Primary Examiner* — Elmer Chao
(74) *Attorney, Agent, or Firm* — Oblon, Spivak, McClelland, Maier & Neustadt, L.L.P.

(57) ABSTRACT

A transmitter/receiver scans a subject body with ultrasonic waves via an ultrasonic probe and obtains first ultrasonic data composed of ultrasonic data in a first coordinate system that is along a scanning line, and a coordinate conversion part included in an image generator performs an arithmetical operation by a GPU and converts the first ultrasonic data from the first coordinate system to a second coordinate system for image display.

12 Claims, 8 Drawing Sheets

BACKGROUND ART

BACKGROUND ART

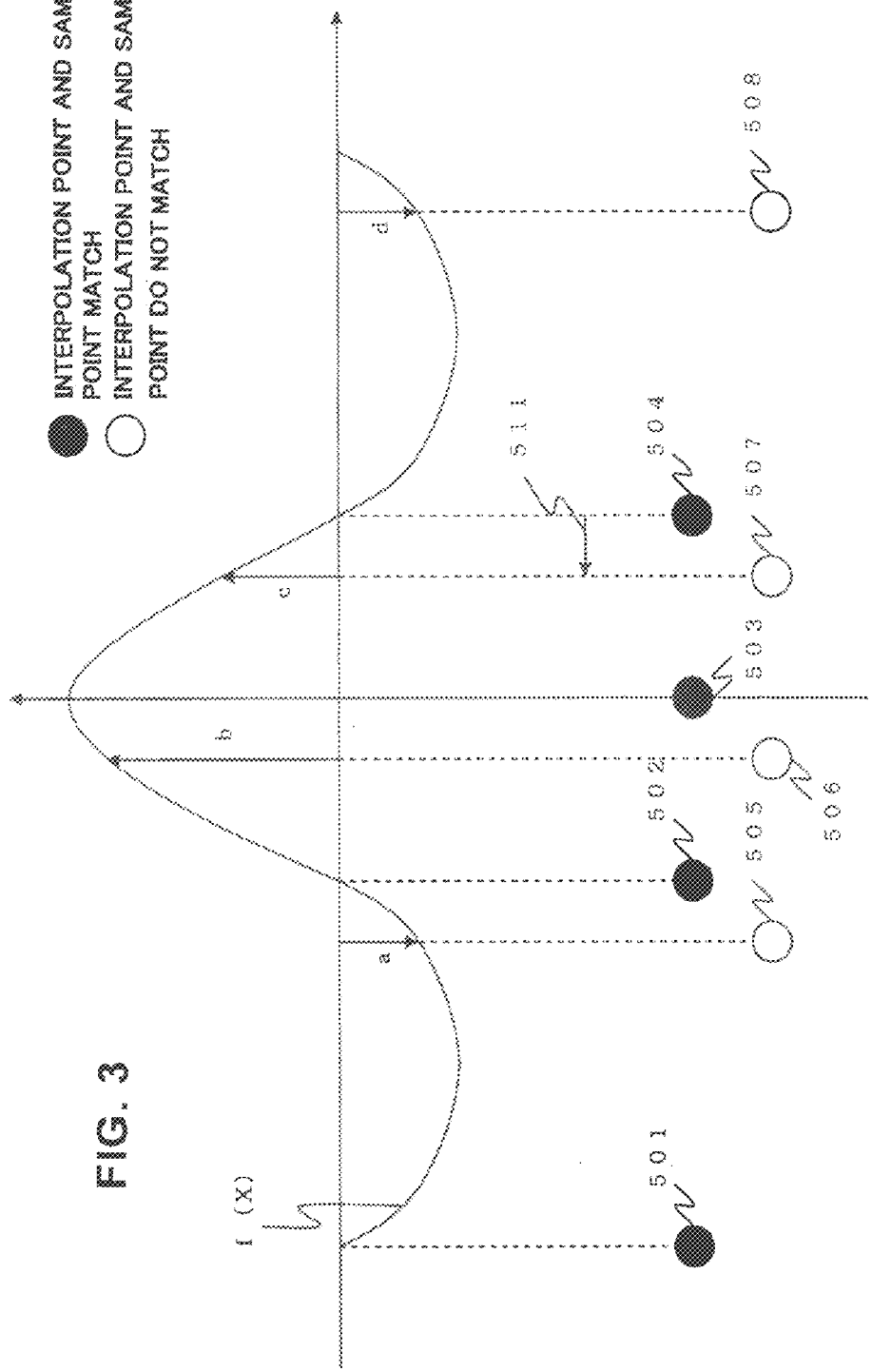

BACKGROUND ART

ULTRASONIC IMAGING APPARATUS AND A METHOD FOR DISPLAYING DIAGNOSTIC IMAGES

BACKGROUND OF THE INVENTION

1. Field of the Invention

The present invention relates to an ultrasonic imaging apparatus that, at the time of generation of an image based on signals obtained by scanning with ultrasonic waves, displays by performing coordinate conversion from coordinates at the time of scanning to coordinates for display.

2. Description of the Related Art

An ultrasonic imaging apparatus is an apparatus configured to obtain biological information from an ultrasonic image of the inside of a subject body, by repeating transmission and reception of ultrasonic waves between a piezoelectric vibrator installed in an ultrasonic probe and the inside of the subject body and executing a variety of processes. The ultrasonic imaging apparatus is capable of performing diagnoses by the ultrasonic tomography method and diagnoses by the ultrasonic Doppler method.

In diagnosis by the ultrasonic tomography method, a 2-dimensional tomographic image of a subject body is obtained by scanning a cross-section of the inside of the subject body with ultrasonic waves and converting the amplitude of reflected wave signals into luminance. The 2-dimensional tomographic image obtained by the ultrasonic tomography method is referred to as a B-mode image. Data to become the basis of creation of this B-mode image is referred to as B-mode data.

On the other hand, in diagnosis by the ultrasonic Doppler method, the velocity of a bloodstream or tissues inside a subject body is measured by utilizing the Doppler effects of ultrasonic waves, and a bloodstream is displayed as a color 2-dimensional image (hereinafter, may be referred to as a "color Doppler image"). Among the ultrasonic Doppler methods, a method of detecting the velocity of a bloodstream specifically and displaying the bloodstream with color is referred to as the color Doppler method.

Herein, assuming complex Doppler signals obtained after passing received ultrasonic signals through an MTI (Moving Target Indicator) filter that extracts a thing moving faster than a specified velocity are $x_1, x_2, x_3, \ldots$ and $x_N$,
Power P is represented by $P=\Sigma|x_i|^2$
Autocorrelation function $C_1$ is represented by $C_1=\Sigma x_i^* x_{i+1}$ (where $x^*$ is a conjugate complex number),
Velocity V is represented by $V=\tan^{-1} C_1$, and
Dispersion T is represented by $T=1-|C_1|/P$.

Furthermore, a method of displaying by superimposing a color Doppler image obtained by the color Doppler method onto a B-mode image obtained by the ultrasonic tomography method is referred to as the color Doppler tomography method.

Thus, the ultrasonic imaging apparatus transmits and receives ultrasonic beams in a deflected state in a predetermined direction from an almost fixed point by means of a piezoelectric vibrator, and performs an ultrasonic scan while sequentially changing the direction, thereby obtaining data in a 2-dimensional cross-section or in a 3-dimensional space. Then, in order to display on a monitor for image display based on sample points (cf. FIG. 1A) obtained by performing an ultrasonic scan with a coordinate system when the data has been obtained (this coordinate system is a coordinate system of (scanning direction, distance); hereinafter, this coordinate system will be referred to as a "scanning coordinate system," and the coordinates will be referred to as "scanning coordinates"), it is necessary to convert the coordinate system into a Cartesian coordinate system that is a grid of the display monitor (cf. FIG. 1B). Herein, FIG. 1A is a diagram of ultrasonic signals represented by scanning coordinates, and FIG. 1B is a diagram of Cartesian coordinates to become the destination of the conversion. Moreover, FIG. 1C is a conceptual diagram of coordinate conversion in which the scanning coordinates and Cartesian coordinates are superimposed. As shown in FIG. 1C in the superimposed state, there is a need to show points of the scanning coordinates as points of the Cartesian coordinates by coordinate conversion.

Conventionally, the processes of coordinate conversion and interpolation in the ultrasonic imaging apparatus have been performed by dedicated hardware known as a DSC (Digital Scan Converter) (Japanese Unexamined Patent Application Publication No. 11-9603). The interpolation process performed by the DSC will be explained below.

Bi-linear interpolation is performed in the case of interpolation of B-mode data or the respective data of velocity, dispersion and power of a bloodstream composing bloodstream information (hereinafter, when these data are not distinguished from each other, one or a plurality of data may be referred to as ultrasonic data). For example, in the case of bi-linear interpolation in which a kernel size is 2×2 (the kernel size is a size for filtering to perform interpolation; here, a filter is sort of a degree of averaging, and the degree of averaging depends on the number of interpolation points), four points are divided into two groups in the x-direction or y-direction, interpolation is performed between the groups with a normal proportion (linear interpolation), and linear interpolation is further performed by using two points found by the interpolation, whereby interpolation of the original four points is completed. In other words, this is a method of, assuming data of four adjacent points are A, B, C and D, calculating an interpolation value with a formula $(1-\beta)\{(1-\alpha)A+\alpha B\}+\beta\{(1-\alpha)C+\alpha D\}$. Here, $\alpha$ and $\beta$ denote degrees of displacement from the interpolation center in the distance direction and the azimuth direction (X and Y) of the scanning coordinates.

Furthermore, the interpolation process with a 2×4 kernel size will be explained with a case of generating a B-mode image. FIG. 2 is a diagram for explaining the interpolation of B-mode data, and this figure is referred to as texture. FIG. 2A is a diagram showing the obtained B-mode data in the scanning coordinates. FIG. 2B is a diagram showing the Cartesian coordinates to be the destination of the conversion. FIG. 2C is a magnified diagram of the obtained B-mode data in the scanning coordinate system. With reference to the scanning coordinates of the obtained B-mode data shown in FIG. 2A and the information of the Cartesian coordinates to be the destination of the conversion shown in FIG. 2B, corresponding vertices are stored in a temporary storage part in order to convert from the scanning coordinates to the Cartesian coordinates. In other words, the corresponding vertices are combinations such as the correspondence between (0,0) and $(x_0, y_0)$, the correspondence between (0, 1) and $(x_0, y_0)$, the correspondence between (1,0) and $(x_1, y_1)$, and the correspondence between (1, 1) and $(x_2, y_2)$. Here, the scanning coordinates of the B-mode data are represented by a graph in which the scanning direction (v) is taken on the vertical axis and the distance (u) is taken on the horizontal axis, as shown in FIG. 2A. Moreover, the Cartesian coordinates after the conversion are represented by a graph in which the horizontal axis takes the X-coordinate and the vertical axis takes the Y-coordinate, as shown in FIG. 2B.

Here, considering a case in which a point (x,y) in the Cartesian coordinate system is extracted as an interpolation point, a method for calculating a point (u,v) in the scanning coordinate system corresponding to the point (x,y) in the Cartesian coordinate system will be explained.

Upon reception of the point (u,v), original sample points A1, A2, B1, B2, C1, C2, D1 and D2 shown in FIG. 2A, which correspond to the point (u,v), are obtained by truncating points other than points necessary to find the point (u,v), based on the 2×4 kernel size. As shown in FIG. 2C, the sample points are in a row of 2×4. Here, FIG. 2 is a diagram for explaining interpolation in the ultrasonic imaging apparatus according to the present invention. As shown in FIG. 2C, when the distance between B1 and C1 is 1, the ratio of the point (u,v) to the line connecting B1 with B2 shall be dv, and when the distance between A1 and A2 is 1, the ratio of the point (u,v) to the line connecting A1 with D1 shall be du.

Next, bi-linear interpolation with the kernel size of 2×2 is performed for points located at the position of the ratio du between A1 and A2, B1 and B2, C1 and C2, and D1 and D2. Here, since the values in the v-axis direction at the respective interpolation points are the same as those of A1, B1, C1 and D1, this 2×2 interpolation is equivalent to the interpolation between two points. In other words, as interpolation values, (1−du)A1+duA2, (1−du)B1+duB2, (1−du)C1+duC2, and (1−du)D1+duD2 are obtained. These obtained interpolation values are denoted by A3, B3, C3 and D3, as shown in FIG. 2C.

Next, calculation of an interpolation coefficient from the interpolation values A3, B3, C3 and D3 and an interpolation function f(x) will be explained. FIG. 3 is a diagram for explaining calculation of the interpolation coefficient from the interpolation function. The interpolation function f(x) is a function that represents fineness from the coarsest level to the finest level. Here, the interpolation function f(x) shall be an interpolation function for obtaining a fine image. Therefore, as shown in FIG. 3, the function f(x) is given as a function such that, when the x coordinate of the intermediate point of the four interpolation values calculated by the abovementioned 2×2 bi-linear interpolation is 0, the y coordinate will be 0. For example, a point 501, a point 502, a point 503 and a point 504 shown in FIG. 3 represent a case in which the interpolation point and the sample point coincide with each other. When the interpolation point and the sample point do not coincide with each other, for example, in the case of the point (u, v) shown in FIG. 2C, the x coordinate of the point (u,v) is moved to become 0. That is, since the ratio from the point (u,v) actually desired to be interpolated to B3 is dv, the coordinate is moved so that the ratio dv becomes 0 and the point (u,v) coincides with B3. In concrete, the point (u,v) is equivalent to point 506 in FIG. 3, and the interpolation function f(x) is moved in the x-axis direction by a distance 511 (by the ratio dv) so that the x coordinate of point 502 coincides with the x coordinate of point 505, the x coordinate of point 503 coincides with the x coordinate of point 506, and the x coordinate of point 504 coincides with the x coordinate of point 507 (in this case, the x coordinate of point 501 moves to the x coordinate of point 508). Consequently, the values of the y coordinates of the four sample points are found. These values are interpolation coefficients.

Based on the found interpolation coefficients, the interpolation value of (u,v) by A1, A2, B1, B2, C1, C2, D1 and D2 is calculated. The interpolation value is found by:

$$a((1-du)A1+duA2)+b((1-du)B1+duB2)+c((1-du)C1+duC2)+d((1-du)D1+duD2)$$

where du denotes displacement from the interpolation center in the distance direction, and
a, b, c and d denote interpolation coefficients of four points in the azimuth direction.

In order to carry out the interpolation process or the coordinate conversion process with the DSC, it is necessary to create dedicated hardware, which requires cost for development and production. Further, processing with the hardware allows only a process embedded at the time of development, so that it is necessary to create other dedicated hardware when changing the content of the processing or addressing new processing afterwards.

In this context, since the processing speed of CPUs (Central Processing Unit) has increased in recent years, a method in which the CPU handles all processes equivalent to those performed by the DSC by using software has also been formulated. However, a process of displaying by converting an image with a frame rate of 60 frames per second in the CPU imposes a large load on the CPU, so that problems occur such as the slower response of processes other than displaying or the lack of displaying images.

In recent years, a GPU (Graphics Processing Unit) has more frequently been employed in displaying images by computer or the like. Herein, the GPU is an image-processing chip having an image-display function and an arithmetic function such as a shading function and an interpolation function. A GPU used recently also supports a coordinate conversion function, and use of this function makes it possible to reduce the load on a CPU due to the coordinate conversion. However, the interpolation function supported by a GPU is bi-linear interpolation with a 2×2 kernel size at the maximum and is low in processing capability.

In the ultrasonic imaging apparatus, a higher-definition image is required, and therefore, it is necessary to interpolate with a kernel size of a high order, and a kernel size of 2×4 is required at the minimum. In this context, in the ultrasonic imaging apparatus, a difference in image quality is definitely made between interpolation with a 2×2 kernel size and interpolation with a 2×4 kernel size. Therefore, it is difficult to create a desired image only by bi-linear interpolation with a 2×2 kernel size. Thus, it has conventionally been difficult to install a GPU in an ultrasonic imaging apparatus.

Furthermore, in the case of interpolating velocity signals of bloodstream signals (color Doppler image), it is necessary to take aliasing into consideration. The aliasing is a phenomenon in which, when spectrum components representing velocity signals exceed half the repeating frequency of sampling pulses for obtaining data (i.e., exceeds Nyquist frequency), spectrum components are observed as a flow in a negative direction. FIGS. 4A and 4B are diagrams for explaining the aliasing. FIG. 4A is a diagram representing the flow of the bloodstream and ultrasonic signals. FIG. 4B is a graph for representing the relationship between ultrasonic signals and colors. In addition, FIG. 4B is a graph in which velocity and color corresponding to the velocity are taken on the vertical axis, wherein an intermediate value 310 is set to 0, the maximum velocity (value 309) is set to 127 and the minimum speed (value 311) is set to −128. For example, considering a case in which, as shown is FIG. 4A, blood 301 is flowing in the direction of arrow 300, a point 302 in the blood 301 is represented by a point 304 represented by red for a velocity of 100, and a point 303 in the blood 301 is represented by a point 305 represented by blue for a velocity of −100. Herein, a point 305 is represented as the bloodstream in the opposite direction due to aliasing. In a case where normal interpolation is performed at this moment, the interpolation is interpolation between the point 304 and the point 305, resulting in a point 306 represented by black for a velocity of 0. In fact, however, the velocity has changed from 100 (red) to −100 (blue) due to the aliasing phenomenon, and an expected interpolation value is a point 307 for −128 (blue). It is difficult for a low-processing-capability processor to carry out such a special interpolation. In this regard, it has conventionally been difficult to install a GPU in an ultrasonic imaging apparatus.

In addition, for image processing in an ultrasonic imaging apparatus, a process of synthesizing a histological image (B-mode image) and a bloodstream image (color Doppler image) in accordance with predetermined logic to form one image is also required. However, this synthesis practice may vary depending on the values of both the B-mode image and the color Doppler image, and it is difficult to realize by a method, such as alpha blending, of simply superimposing images. In this regard, it has been difficult to install a GPU in an ultrasonic imaging apparatus.

Then, a GPU architecture in earlier periods was only capable of executing a graphics process embedded at the time of development of the GPU, but a recent programmable GPU architecture allows immediate application of a newly developed technology, by updating the system.

SUMMARY OF THE INVENTION

The present invention has been achieved in consideration of the circumstances as described above, and an object of the present invention is to provide an ultrasonic imaging apparatus using a GPU that is capable of displaying high-definition ultrasonic images by performing interpolation by combining hardware and software, and that is programmable for ultrasonic-image processing.

Another object of the present invention is to provide an ultrasonic imaging apparatus that is capable of easily counteracting aliasing in velocity information of a bloodstream by handling velocity, dispersion and power as complex data and calculating.

In a first aspect of the present invention, a transmitter/receiver configured to scan a subject body with ultrasonic waves via an ultrasonic probe, and obtain first ultrasonic data composed of ultrasonic data in a first coordinate system that is along a scanning line, and a coordinate conversion part configured to perform an arithmetical operation by a GPU, and convert the first ultrasonic data from the first coordinate system to a second coordinate system for image display are provided. This technique can be applied to an ultrasonic imaging apparatus.

In a second aspect of the present invention, a transmitter/receiver configured to scan a subject body with ultrasonic waves via an ultrasonic probe and obtain first ultrasonic data composed of ultrasonic data in a first coordinate system that is along a scanning line, and a coordinate conversion part configured to perform an arithmetical operation by a processor that is capable of performing parallel processing and is programmable and convert the first ultrasonic data from the first coordinate system into a second coordinate system for image display are provided. This technique can be applied to an ultrasonic imaging apparatus.

In a third aspect of the present invention, scanning a subject body with ultrasonic waves via an ultrasonic probe and obtaining first ultrasonic data composed of ultrasonic data in a first coordinate system that is along a scanning line, and performing an arithmetical operation by a GPU and performing coordinate conversion of the first ultrasonic data from the first coordinate system to a second coordinate system for image display are performed. This technique can be applied to a method for displaying diagnostic images.

According to the aspects described above, it is possible to execute fast processing by performing with the hardware a fundamental part of the interpolation for displaying ultrasonic signals in the Cartesian coordinate system, as well as perform a part thereof with a program. Therefore, by programming this program, it is possible to perform interpolation with various interpolation functions. Consequently, the need to develop dedicated hardware executing interpolation is eliminated, which makes it possible to reduce cost. Further, it is facilitated to change the content of a process and address a new process.

BRIEF DESCRIPTION OF THE DRAWINGS

FIG. 3 is a diagram for explaining calculation of an interpolation coefficient from an interpolation function.

DETAILED DESCRIPTION OF THE EMBODIMENTS

First Embodiment

Figure 5:
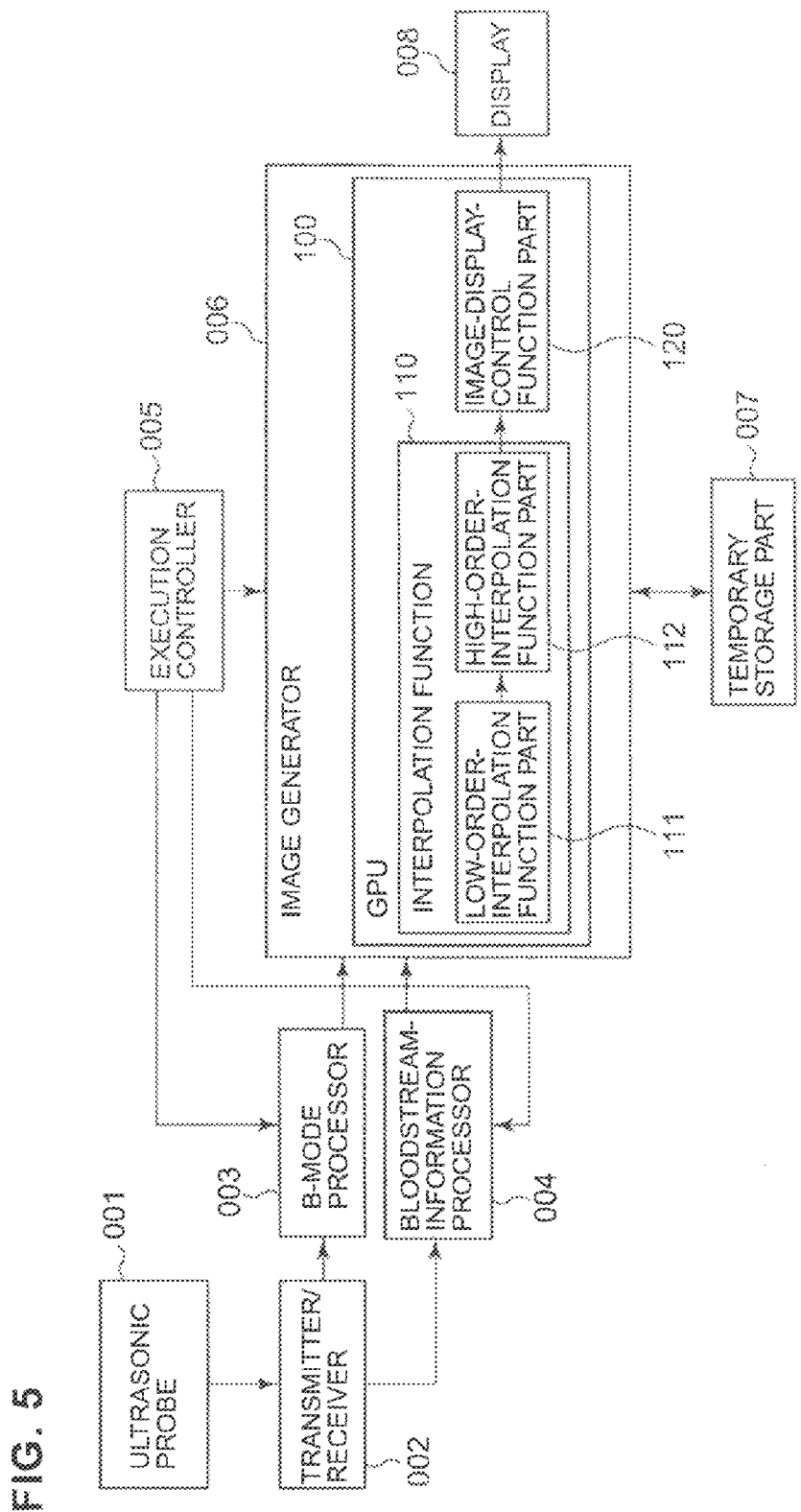
FIG. 5 is a block diagram of the ultrasonic diagnostic apparatus according to an embodiment of the present invention.

An ultrasonic imaging apparatus according to a first embodiment of the present invention will be explained below. FIG. 5 is a block diagram showing functions of the ultrasonic imaging apparatus according to an embodiment of the present invention. Here, a B-mode processor 003, a bloodstream-information processor 004, and an execution controller 005 in FIG. 5 are each composed of a CPU. Further, an image generator 006 is composed of a GPU 100, and the GPU 100 has an interpolation function part 110 that performs interpolation for conversion from scanning coordinates to Cartesian coordinates and an image-display-control function part 120. Here, the scanning coordinate system is equivalent to a "first coordinate system" of the present invention. Further, the Cartesian coordinate system is equivalent to a "second coordinate system" of the present invention. This GPU 100 is a programmable processor capable of executing parallel processing. In addition, the GPU 100 has an image-display function such as graphic drawing, and an arithmetic function such as a shading function and an interpolation function. Furthermore, the interpolation function part 110 has two functions: a low-order-interpolation function part 111 and a high-order-interpolation function part 112. Here, the low-order-interpolation function part 111 performs an arithmetical operation on a fundamental part of interpolation of ultrasonic data by means of hardware of the GPU 100 or micro cord of the GPU 100. Further, the high-order-interpolation function part 112 performs higher-order interpolation by using values computed by the hardware based on a program for a shading process programmed in advance. This shading process is typically a process of deformation and movement of an image and effects of colors. A major process of the shading process in the present invention is to perform interpolation and coordinate conversion. In the ultrasonic imaging apparatus according to the present invention, the execution controller 005 actually controls the entire apparatus. However, for convenience, an explanation may be made below as if the respective parts directly exchange information. Thus, the GPU 100 performs simple interpolation with the hardware or micro cord, and performs advanced interpolation with a program.

A transmitter/receiver 002 transmits ultrasonic signals received via an ultrasonic probe 001, to the B-mode processor 003 and the bloodstream-information processor 004.

The B-mode processor 003 converts the obtained ultrasonic signals into B-mode data. Here, data obtained as the B-mode data contains information on intensity at a position represented by coordinates of the scanning direction and distance.

Next, the B-mode processor 003 transmits the obtained B-mode data to the image generator 006.

The bloodstream-information processor 004 converts the obtained ultrasonic signals into data of velocity, dispersion and power of a bloodstream (hereinafter, simply referred to as "velocity, dispersion and power") that compose bloodstream information. Here, data obtained as the bloodstream information is calculated based on complex Doppler signals obtained from the detected ultrasonic signals, as explained in background of the invention.

Next, the bloodstream-information processor 004 transmits data of velocity, dispersion and power that constitute the obtained bloodstream information to the image generator 006.

Hereinafter, data that has been transmitted from the B-mode processor 003 and the bloodstream-information processor 004 to the image generator 006 and has not been subjected to image processing may be referred to as original data. This original data is equivalent to "first ultrasonic data" of the present invention. Then, coordinates in the scanning direction and distance that represent the first ultrasonic data constitute the first coordinate system.

The execution controller 005 transmits a kernel size and an interpolation function that have been inputted by an operator to the image generator 006. Here, the kernel size shall be 2×4, and the interpolation function shall be f(x).

The image generator 006 causes a temporary storage part 007 to store the received B-mode data or data of velocity, dispersion and power that constitute the bloodstream information. Based on the data stored in the temporary storage part 007, the image generator 006 then performs coordinate conversion and interpolation for causing a display 008 to display the B-mode data or the data of velocity, dispersion and power that constitute the bloodstream information. Hereinafter, coordinate conversion, interpolation, and image display by the image generator 006 will be explained in detail for each of the B-mode data and the bloodstream information.

B-Mode Data

Figure 1A:
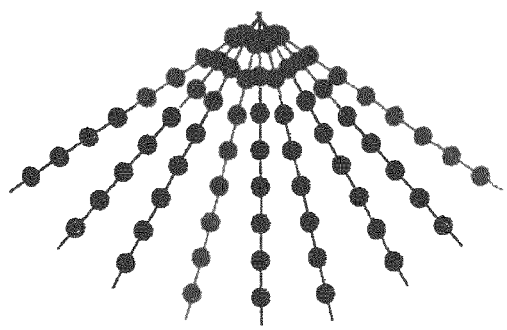
FIG. 1A is a diagram for explaining ultrasonic data in the scanning coordinates.
Figure 1B:
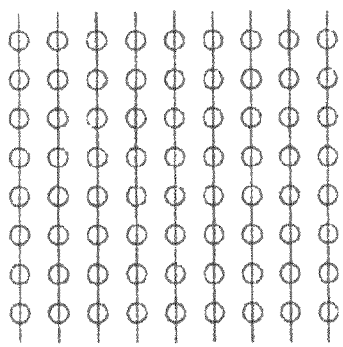
FIG. 1B is a diagram for explaining the Cartesian coordinates of the destination for conversion.
Figure 1C:
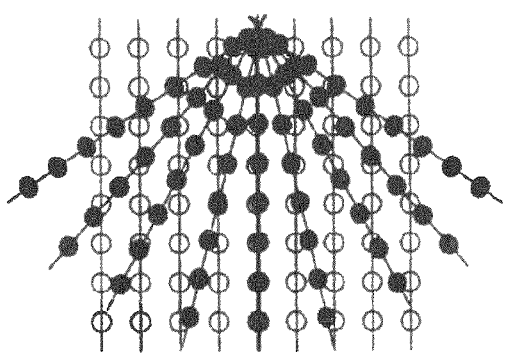
FIG. 1C is a diagram for explaining conversion from the scanning coordinates to the Cartesian coordinates.
Figure 2A:
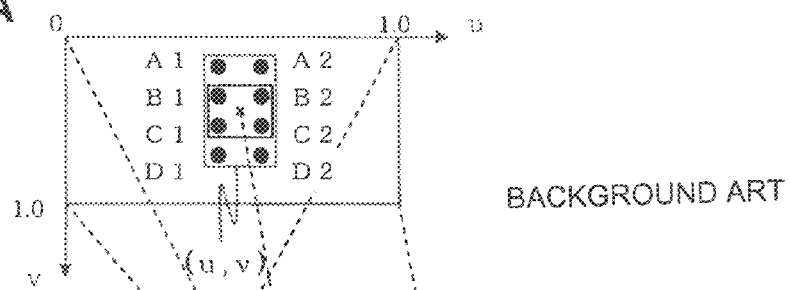
FIG. 2A is a diagram representing the obtained B-mode data in the scanning coordinates.
Figure 2B:
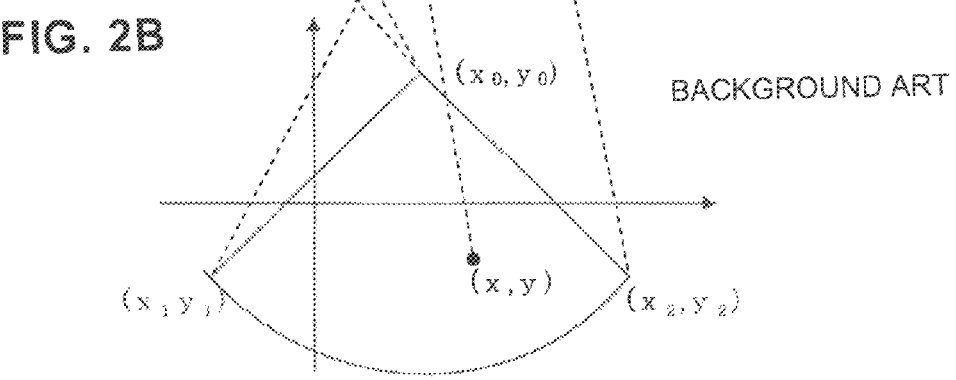
FIG. 2B is a diagram representing the Cartesian coordinates of the destination for conversion.

The GPU 100 refers to position information in the scanning coordinates of the received B-mode data shown in FIG. 2A and information of the Cartesian coordinates of the destination for the conversion shown in FIG. 2B, and causes the temporary storage part 007 to store corresponding vertices in order to convert from the B-mode data position information into the Cartesian coordinates. Here, data in which the respective vertexes are made to correspond to each other in order to convert the B-mode data position information to the Cartesian coordinates is "geometric conversion data" that makes the "first coordinate system" and the "second coordinate system" correspond to each other in the present invention.

The GPU 100 extracts a point to interpolate. Next, considering a case of extracting a point (x,y) in the Cartesian coordinate system as the point to interpolate, the GPU 100 calculates a point (u,v) in the scanning coordinate system corresponding to the point (x,y) in the Cartesian coordinate system.

The execution controller 005 controls the low-order-interpolation function part 111 in the following manner, as a first step for performing interpolation with the 2×4 kernel size.

Figure 2C:
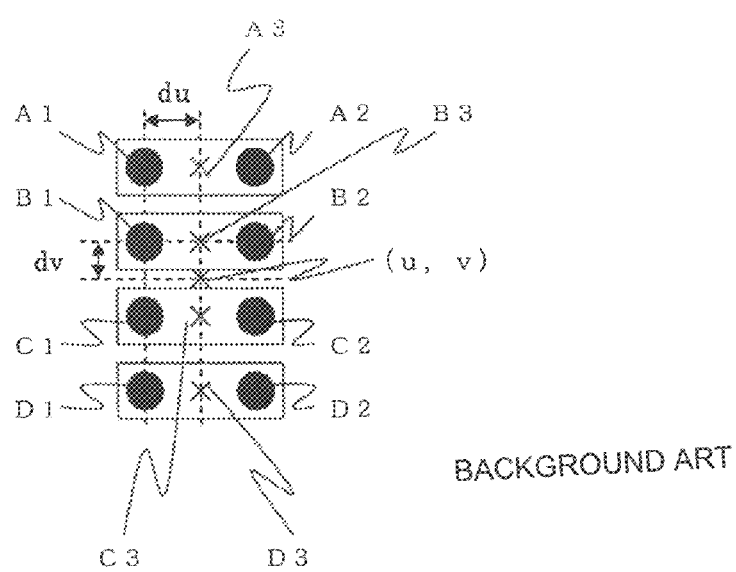
FIG. 2C is a magnified diagram of the obtained B-mode data in the scanning coordinates.

Upon receiving the point (u,v), the low-order-interpolation function part 111 obtains sample points A1, A2, B1, B2, C1, C3, D1 and D2 in the original data shown in FIG. 2A, corresponding to the point (u,v), by truncating points other than the points necessary to find the point. As shown in FIG. 2C, when the distance between B1 and C1 is 1, the ratio of the point (u,v) to the line connecting B1 with B2 shall be dv, and when the distance between A1 and A2 is 1, the ratio of the point (u,v) to the line connecting A1 with D1 shall be du.

Assuming dv=0, the low-order-interpolation function part 111 performs bi-linear interpolation with the kernel size of 2×2 for points that are located at the position of the ratio du between A1 and A2, B1 and B2, C1 and C2, and D1 and D2. Here, since the respective interpolation points have the same values in the v-axis direction as A1, B1, C1 and D1, this 2×2 interpolation is equivalent to interpolation between two points. In other words, the low-order-interpolation function part 111 calculates, as interpolation values, A3=(1−du)A1+duA2, B3=(1−du)B1+duB2, C3=(1−du)C1+duC2, and D3=(1−du)D1+duD2.

The ultrasonic imaging apparatus in the present embodiment performs the arithmetical operation for the interpolation by using the GPU, so that it is possible to use floating decimal points in the arithmetical operation for finding an interpolation point. Therefore, it is possible to find the ratio du for finding an interpolation point with accuracy up to the digit of the floating decimal point, whereby it is possible to increase the accuracy in interpolation by the digit of the floating decimal point as compared with conventional interpolation using fixed points.

The low-order-interpolation function part 111 transmits the calculated interpolation values A3, B3, C3 and D3 to the high-order-interpolation function part 112.

As a step for performing interpolation with 2×4 kernel size, the execution controller 005 controls the high-order-interpolation function part 112 in the following manner.

Upon receiving the interpolation function f from the execution controller 005, the high-order-interpolation function part 112 finds interpolation coefficients a, b, c and d of the respective four interpolation values calculated by the low-order-interpolation function part 111. Here, the interpolation function f is a function of dv, and represented by (a, b, c, d)=f(dv). In the process so far, the process content itself is similar to the conventional process, but in the present embodiment, it is possible to perform the process at high speed by performing this process with the hardware of the GPU 100.

The high-order-interpolation function part 112 calculates an interpolation value based on the derived interpolation coefficient. This interpolation value is found by aA3+bB3+cC3+dD3.

The high-order-interpolation function part 112 transmits the calculated interpolation value to the image-display-control function part 120.

The image-display-control function part 120 converts into RGB data for display color and tone based on data of the interpolation value by using an LUT (Look Up Table), and makes the RGB data displayed at a point (x,y) in the Cartesian coordinate system on the display 008.

The image generator 006 performs the above-described interpolation tasks for the number of required points, and then causes the display 008 to display a B-mode image based on the obtained B-mode data.

Blood Stream Information

With the LUT, the GPU 100 finds complex data having a real term Re and an imaginary term Im from the velocity (V), the dispersion (T) and the power (P) that constitute the bloodstream information, by employing the following formula.

$$Re=((255-T)/2)\cos(\pi V/128)$$

$$Im=((255-T)/2)\sin(\pi V/128)$$

Here, for a coefficient, the value of the coefficient in the above formula is employed because 8-bit signals are used for processing. However, this coefficient varies depending on the signals to be used and therefore, is not limited to this value.

The GPU 100 finds an interpolation value by causing the interpolation function part 110 to perform interpolation for converting the data composed of three values of Re, Im and P, from the scanning coordinates in which Re is taken on the X axis and Im is taken on the Y axis, into Cartesian coordinates. This interpolation method is performed on each of Re, Im and P in the same manner as the method explained for the B-mode data.

Figure 4A:
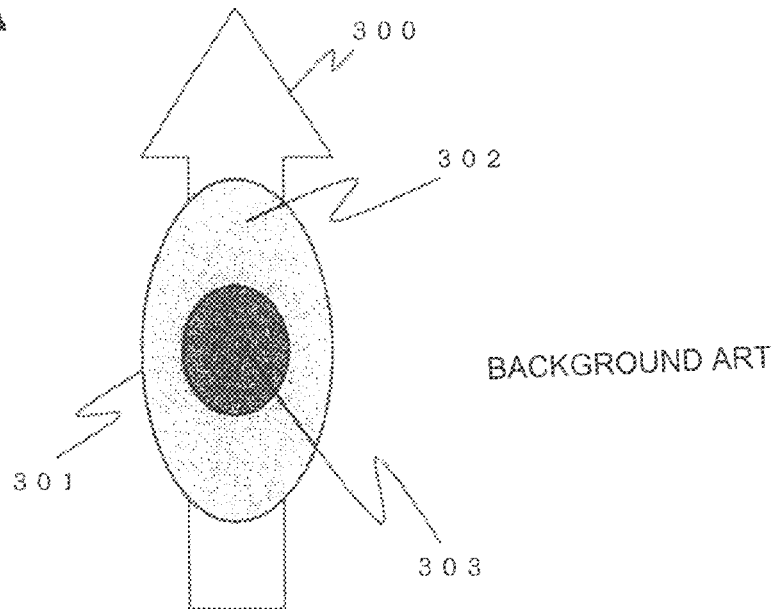
FIG. 4A is a diagram representing the flow of a bloodstream and ultrasonic signals.
Figure 4B:
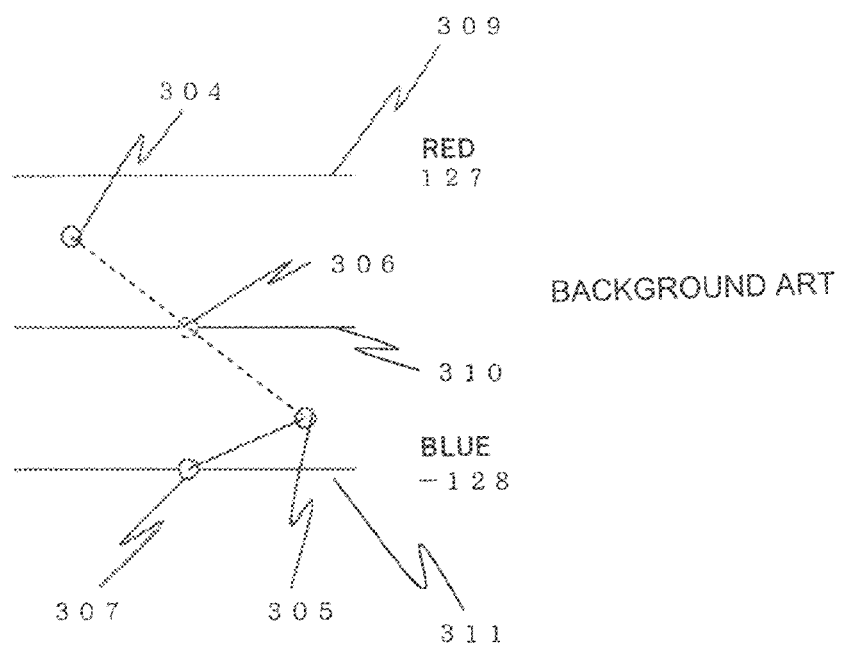
FIG. 4B is a graph for representing the relationship between ultrasonic signals and colors.
Figure 6:
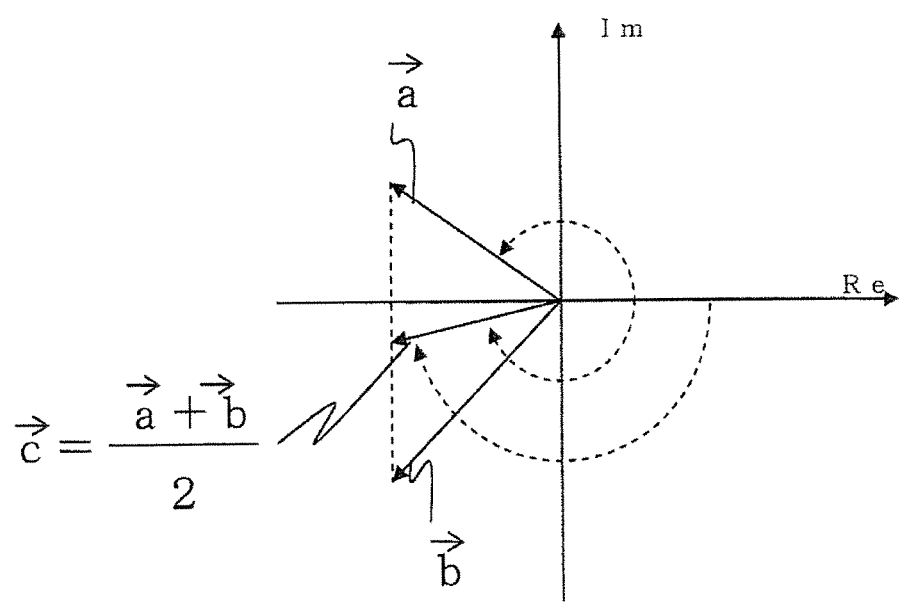
FIG. 6 is a diagram for explaining a method of interpolating blood velocity using complex numbers.

Given the complex number Re+jIm, by taking the values at the same positions as the interpolated Re and Im, the deflection angle thereof is the interpolated velocity. As shown in FIG. 6, an interpolation vector of two vectors—vector a and vector b—near the aliasing velocity is vector c, so that almost the same results as in the interpolation shown in FIG. 4 are obtained. FIG. 6 is a diagram for explaining the method of interpolating blood velocity using complex numbers. Furthermore, with reference to the above Re and Im, this interpolation will be performed with the function $1-T=|C_1|/P$. Moreover, as explained in the background of the invention, it is represented as $P=\Sigma x_i|^2$ and $C_1=\Sigma x_i^* x_{i+1}$, so that as C1 becomes larger, P also becomes larger. In other words, 1−T can be kept to a certain size, so that the dynamic range can be kept small, whereby it is possible to facilitate interpolation.

In addition, the GPU 100 can cause the interpolation function part 110 to perform interpolation of frames. The interpolation of frames is to insert an interpolation frame between color Doppler images that have actually been scanned and generated in order to make the temporal appearance of the color Doppler image look smooth, wherein the frame rate tends to be slow. This interpolation is also performed by utilizing the values of Re, Im and P. This interpolation is performed using a linear interpolation between two frames. Furthermore, the interpolation function part 110 finds the interpolation value of velocity (V), dispersion (T), and power (P), based on the derived interpolation value of Re and Im.

Next, the GPU 100 executes a coloring process of the original data and the interpolated data. This process is a process for making the obtained data visible. This process varies depending on which information of the velocity (V), dispersion (T), and power (P) constitutes the information to be displayed by the color Doppler image (hereinafter, referred to as "display mode").

When the display mode of the color Doppler image is the velocity (V) and dispersion (T), the GPU 100 calculates V and T from the following formula.

$$V=(128/\pi) \text{ atan } 2(im,Re)$$

$$T=255-2\sqrt{(Re^2+Im^2)}$$

$$P=(1-|C_1|)/T$$

Here, atan 2 is an arctangent function for finding an angle in the range of −π to π.

The interpolation velocity obtained by the interpolation as described above is similar to the velocity by conventional interpolation that is measured against aliasing to a degree of difficulty to identify on an image, so that it can be said that this interpolation has sufficient accuracy.

Next, the GPU 100 causes the image-display-control function part 120 to convert, by using the LUT, the obtained velocity (V) and dispersion (T) into the RGB data of a color and tone, and causes the display 008 to display.

When a mode of displaying the color Doppler image is power (P), it is determined by the original power value or the interpolated power (P) value. The GPU 100 then causes, by using LUT, the image-display controller 120 to convert the power (P) into the RGB of color and tone, and causes the display 008 to display.

As described above, in the case of creating a color Doppler image, it is necessary to perform interpolation for three sets of data—velocity (V), dispersion (T), and power (P). In addition, the image-display-control function part 120 of the GPU 100 has a parallel circuit capable of processing four sets of data—red, blue, green and alpha—in parallel in the process of image display. Therefore, to interpolate in parallel by processing three sets of data—velocity (V), dispersion (T), and power (P)—in three parallel processing circuits for processing the colors of red, blue, and green, respectively.

Here, the "coordinate conversion part" of the present invention includes the interpolation function part 110, and performs the interpolation and coordinate conversion by the GPU 100 as explained above. In addition, the coordinate conversion part is one of the constituent elements of the image-forming part 006.

Figure 7:
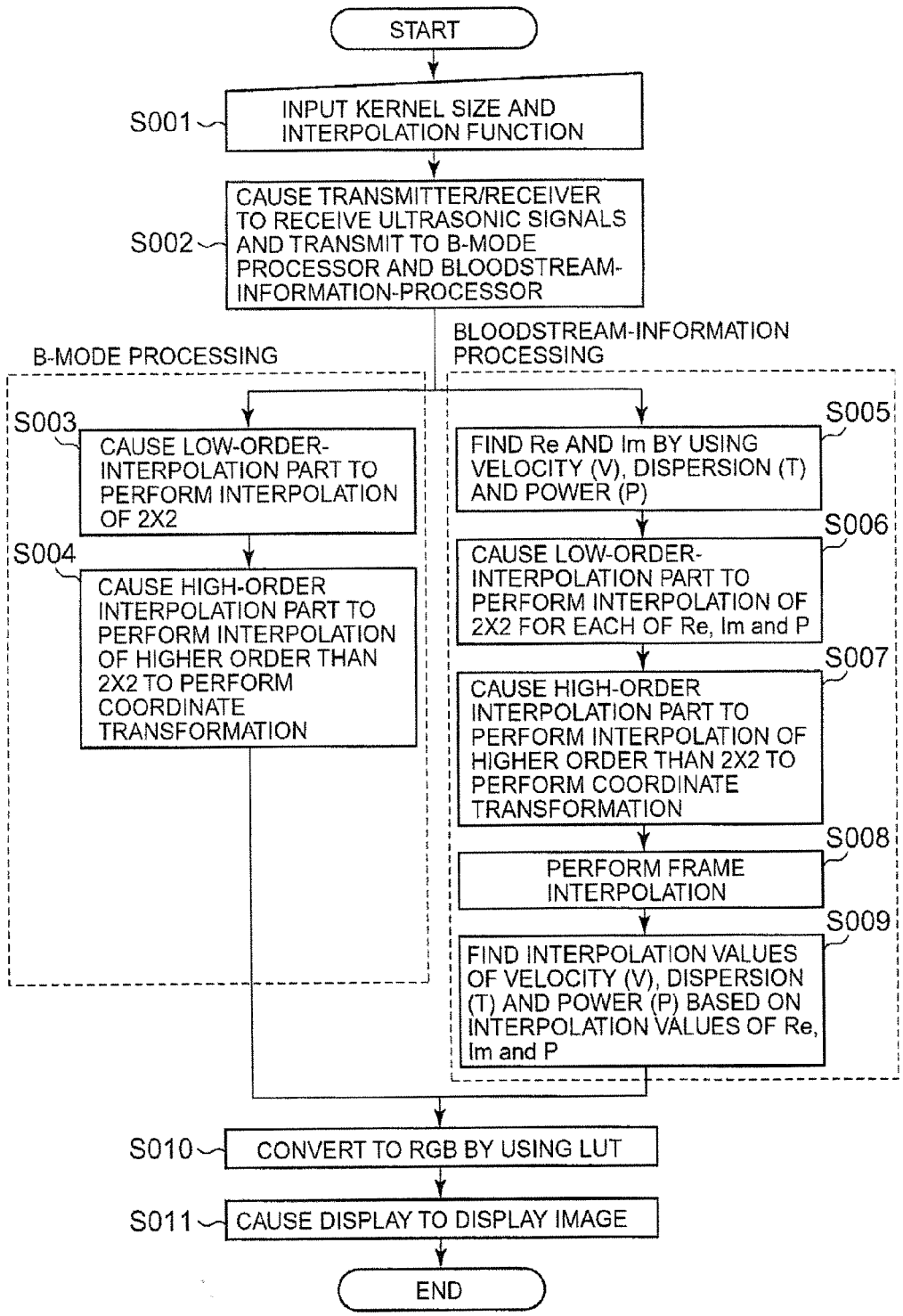
FIG. 7 is a flowchart of image formation in the ultrasonic diagnostic apparatus according to a first embodiment.

Next, the flow of forming an ultrasonic image according to the present embodiment will be explained with reference to FIG. 7. Here, FIG. 7 is a flow chart of forming an ultrasonic image according to the present embodiment.

Step S001: An operator inputs a kernel size and an interpolation function.

Step S002: The transmitter/receiver 002 transmits the ultrasonic signals received via the ultrasonic probe 001 to the B-mode processor 003 and the bloodstream-information processor 004.

(B-Mode Processing)

Step S003: the low-order-interpolation function part 111 causes the temporary storage part 007 to store the B-mode data transmitted thereto, refers to the inputted kernel size to perform 2×2 interpolation based on the B-mode data stored in the temporary storage part 007, and transmits the interpolation value to the high-order-interpolation function part 112.

Step S004: The high-order-interpolation function part 112 refers to the interpolation function to calculate an interpolation coefficient, performs higher-order interpolation than 2×2 by using the interpolation coefficient. Then, the interpolation part 110 transmits the interpolation value and the original data used without change, to the image-display controller 120.

(Bloodstream-Information Processing)

Step S005: The GPU 100 causes the temporary storage part 007 to store the data of velocity (V), dispersion (T) and power (P) that constitute the bloodstream information transmitted thereto, and finds Re and Im based on the data.

Step S006: The low-dimensional interpolation part 111 refers to the inputted kernel size to perform 2×2 interpolation based on the found Re and Im, and transmits the interpolation value to the high-order-interpolation function part 112.

Step S007: The high-order-interpolation function part 112 calculates an interpolation coefficient by referring to the interpolation function, and performs higher-order interpolation than 2×2, such as 2×4 interpolation, by using the interpolation coefficient.

Step S008: The interpolation function part 110 performs frame interpolation.

Step S009: The interpolation function part 110 finds an interpolation value of velocity (V), dispersion (T) and power (P), based on the interpolation value of the Re and Im, and transmits, to the image-display controller 120, the data of the interpolation value and the original data to be used without change.

(B-Mode Processing and Bloodstream-Information Processing)

Step S010: the image-display-control function part 120 converts the transmitted data into RGB by using LUT.

Step S011: The image-display-control function part 120 causes the display 008 to display an image based on the converted value of RGB.

As described above, in the ultrasonic imaging apparatus according to the present invention, it is possible to, by employing a normal GPU, perform interpolation with a kernel size up to 2×2 by using the low-order-interpolation function part 111 with hardware or micro cord of the GPU at high speed and, based on the interpolation value, perform interpolation with a 2×4 kernel size programmatically by using the high-order-interpolation function part 112. Consequently, it is possible to reduce the cost, and facilitate an update of process content and handling of a new process because it is possible to freely program an interpolation process. Further, since a versatile GPU can be employed, it is possible to keep the expenditure for manufacturing the ultrasonic imaging apparatus small, thereby reducing the cost. Furthermore, it also becomes possible to reduce the development cost of the ultrasonic imaging apparatus. In addition, the GPU performs an interpolation-arithmetic operation, so that it is possible to execute interpolation by the arithmetic operation of floating decimal point with just the processing capacity of the GPU. Consequently, it becomes possible to increase the interpolation accuracy by just a digit of the floating decimal point corresponding to the processing capacity of the GPU, and increase the quality of an ultrasonic tomographic image to be generated. Moreover, since it is possible to execute coordinate conversion by a geometric conversion of the GPU, it is possible to execute coordinate conversion that cannot be derived from conversion from the polar coordinates to the Cartesian coordinates (coordinate conversion that cannot be represented by a mathematical formula). Therefore, it becomes possible to perform, with ease and high accuracy, a scan using a special probe or a 2-dimensional array probe that requires the coordinate conversion that cannot be derived from the conversion from the polar coordinates to the Cartesian coordinates. Furthermore, processes of the velocity, dispersion and power of the bloodstream can be arithmetically calculated simultaneously by, for example, assigning them to systems of processing R, G and B that the GPU has as parallel processing systems, whereby it becomes possible to simplify the configuration because the need to have three systems of the same circuits can be eliminated, and it becomes possible to suppress the cost. Moreover, parallel processing enables increase of the processing speed.

Second Embodiment

Hereinafter, an ultrasonic imaging apparatus according to a second embodiment of the present invention will be explained. The ultrasonic imaging apparatus in the present embodiment is configured to, in the first embodiment, perform a process of synthesizing the generated B-mode image and color Doppler image and display in the superimposed state. Now, a process of synthesizing the B-mode image and the color Doppler image will be explained. Here, the ultrasonic imaging apparatus of the present embodiment also has the functional block shown in FIG. 5. The synthesizing process is executed by the GPU 100.

The image-display-control function part 120 of the GPU 100 has four parallel processing circuits: red, blue, green and alpha. In a normal usage of the processing circuits, the GPU 100 processes colors in the first three processing circuits and processes opacity in the alpha processing circuit. In the present invention, the GPU 100 employs a processing circuit that processes red, blue and green as a processing circuit used for creating a B-mode image or a color Doppler image, and hence, it does not use a circuit that processes alpha data. Then, in the ultrasonic imaging apparatus of the present embodiment, threshold information tailored to image conditions is stored in advance in the processing circuit that processes the alpha data among the abovementioned four parallel processing circuits—red, blue, green and alpha—in the image-display-control function part 120 of the GPU 100.

This threshold information refers to a certain value for executing a process of not displaying a B-mode image when the B-mode data is a certain value or less or a certain value or more, and a process of not displaying a color Doppler image when the value of the bloodstream information is a certain value or less or a certain value or more. For example, in the case of generation of an ultrasonic image of a heart, there should be a heart wall and no bloodstream at a portion where the luminance of the value of the B-mode data is high, so that the bloodstream information of the portion is recognized as noise. Therefore, there is a need to delete the color Doppler image at the portion needs. Alternately, in the case of generation of an ultrasonic image of an abdomen, information on the bloodstream is important, so that there is a need to display the bloodstream unconditionally when the bloodstream is a certain level or more. Thus, when the bloodstream is a certain level or less, there is a need to delete as noise. Furthermore, when the power value is low, it is likely to be noise, so that it is necessary not to display a color Doppler image. Thus, when overlapping, it is necessary to execute a synthesis process depending on various conditions, so that it is necessary to store image conditions and threshold information.

The image-control-display function 120 of the GPU 100 receives, from the high-order-interpolation function part 112, the B-mode data and data of the velocity (V), dispersion (T) and power (P) constituting the bloodstream information, refers to the image conditions and threshold information stored in the circuit that processes alpha data, and determines which data will be displayed at each point.

The image-control-display function 120 converts, by using the LUT, the received B-mode data, data of the velocity (V), dispersion (T) and power (P) constituting bloodstream information, and the determination as to which data will be displayed at each point, into the RGB data of a color and tone to be displayed, and displays, on the display 008, an image in which a B-mode image and color Doppler image are synthesized.

The explanation above has been given for a case of displaying either a B-mode image or a color Doppler image in preference to another, but it may be a configuration to display the both under certain conditions. For example, in order to display the B-mode data and one of the bloodstream information (herein, the velocity (V)) so that the B-mode data is overlapped with the data of the velocity (V) and can be seen translucently, the image-display-control function part 112 transmits both the B-mode data and the data of the velocity (V) to the processing circuit for alpha data to calculate what degree of transparency the B-mode data has and perform the synthesizing process, then converts into RGB data by using the LUT, and causes the display 008 to display.

Figure 8:
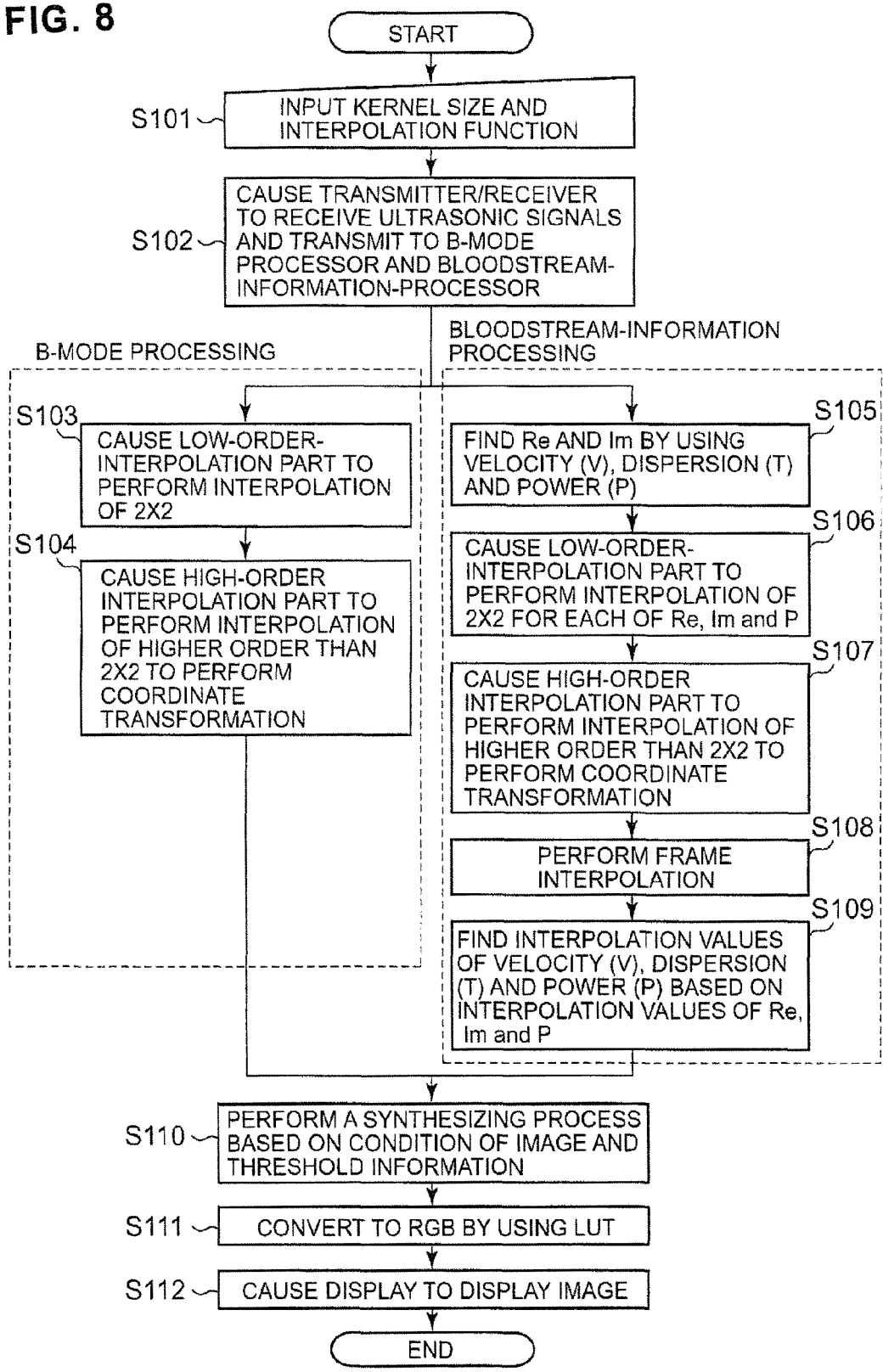
FIG. 8 is a flowchart of image formation in the ultrasonic diagnostic apparatus according to a second embodiment.

Next, the flow of formation of an ultrasonic image according to the present embodiment will be explained with reference to FIG. 8. Herein, FIG. 8 is a flowchart of formation of an ultrasonic image according to the present embodiment.

Step S101: An operator inputs a kernel size and an interpolation function.

Step S102: The transmitter/receiver 002 transmits the ultrasonic signals received via the ultrasonic probe 001 to the B-mode processor 003 and the bloodstream-information processor 004.

(B-Mode Processing)

Step S103: the low-order-interpolation function part 111 stores the transmitted B-mode data on the temporary storage part 007, references the inputted kernel size, performs 2×2 interpolation based on the B-mode data on the temporary storage part 007, and transmits the interpolation value thereof to the high-order-interpolation function part 112.

Step S104: The high-order-interpolation function part 112 calculates an interpolation coefficient with reference to the interpolation function, performs higher-dimensional interpolation than 2×2 by employing the interpolation coefficient, and the interpolation part 110 transmits, to the image-display controller 120, the interpolation value and the original data to be used without change.

(Bloodstream-Information Processing)

Step S105: The GPU 100 causes the temporary storage part 007 to store data of the velocity (V), dispersion (T) and power (P) that constitute the bloodstream information transmitted thereto, and finds Re and Im based on the data.

Step S106: The low-dimensional interpolation part 111 refers to the inputted kernel size, performs 2×2 interpolation based on the found Re and Im, and transmits the interpolation value to the high-order-interpolation function part 112.

Step S107: The high-order-interpolation function part 112 calculates an interpolation coefficient with reference to the interpolation function, and performs higher-order interpolation than 2×2 by using the interpolation coefficient.

Step S108: The interpolation function part 110 performs frame interpolation.

Step S109: The interpolation function part 110 finds an interpolation value of the velocity (V), dispersion (T) and power (P), based on the interpolation value of the Re and Im, and transmits data of the interpolation value and the original data used without change, to the image-display controller 120.

(B-Mode Processing and Bloodstream-Information Processing)

Step S110: The image-display controller 120 determines data to be displayed, based on the image conditions and the threshold information stored in the processing circuit of alpha data.

Step S111: The image-display controller 120 converts the determined data into RGB by using LUT.

Step S112: The image-display controller 120 causes the display 008 to display an image, based on the converted value of RGB.

As described above, in the case of performing a synthesizing process by superimposing a B-mode image and a color Doppler image, it is possible to perform the synthesizing process in parallel with creating images, by using a circuit that processes alpha data of the GPU. Consequently, it becomes possible to process at a high speed and display a complex image such as a synthetic image, whereby it is possible to contribute to increase of the effects of ultrasonic diagnoses.

What is claimed is:

1. An ultrasonic imaging apparatus, comprising:
a transmitter/receiver configured to scan a subject body with ultrasonic waves via an ultrasonic probe, and to obtain first ultrasonic data including ultrasonic data in a first coordinate system that is along a scanning line;
an image generator including a graphics processing unit (GPU), the GPU including a coordinate conversion part configured to perform an arithmetical operation, and to convert the first ultrasonic data from the first coordinate system to a second coordinate system for image display;
a B-mode processor configured to generate B-mode data as a portion of the first ultrasonic data and to cause the image generator to generate converted B-mode data; and
a bloodstream information processor configured to generate velocity, dispersion, and power data as an additional portion of the first ultrasonic data and to cause the image generator to generate converted velocity, dispersion, and power data, wherein
the GPU includes an image display controller configured to synthesize the converted B-mode data with the converted velocity, dispersion, and power data, and to determine a combination of the B-mode data and the converted velocity, dispersion, and power data to be displayed at each point, based on image conditions and threshold information,
the image display controller includes exactly four parallel processing circuits, including three parallel processing circuits and an alpha circuit, wherein, in one mode, the three parallel processing circuits are configured to process color and the alpha circuit is configured to process opacity, and in another mode, the alpha circuit stores the threshold information and is configured to perform the synthesizing process to synthesize the B-mode data and the velocity, dispersion, and power data, and the three parallel processing circuits are configured to generate B-mode images and generate Doppler images from the velocity, dispersion, and power data in parallel with the synthesizing process performed by the alpha circuit,
the coordinate conversion part is further configured to perform an interpolation arithmetical operation of interpolating one point in the second coordinate system, based on a plurality of points in the first coordinate system, and
in performing the interpolation arithmetical operation, upon reception of an input of a kernel size that is a size for filtering, the kernel size being a higher order than 2×2, low-order 2×2 bi-linear interpolation is performed by a hardware circuit of the GPU to determine first interpolation values, and a second interpolation value is found by executing a program loaded by a programmable processor of the GPU that implements higher-order interpolation than 2×2, based on the determined first interpolation values and a predetermined interpolation function.

2. The ultrasonic imaging apparatus according to claim 1, wherein
the coordinate conversion part is configured to obtain geometric conversion data that makes the first coordinate system correspond to the second coordinate system, and the GPU is configured to perform geometric conversion based on the geometric conversion data and to perform the coordinate conversion.

3. The ultrasonic imaging apparatus according to claim 1, wherein
the first ultrasonic data includes a plurality of types of bloodstream information; and
the coordinate conversion part is configured to simultaneously perform a plurality of coordinate conversions of the plurality of types of bloodstream information.

4. The ultrasonic imaging apparatus according to claim 1, wherein
the coordinate conversion part is configured to determine a complex number whose elements are the velocity, dispersion, and power data of a bloodstream included in the first ultrasonic data, to calculate an interpolation value of the complex number, and thereafter, to convert the velocity, dispersion, and power data of the bloodstream individually based on the interpolation value to determine an interpolation value of the velocity, dispersion, and power data of the bloodstream.

5. The ultrasonic imaging apparatus according to claim 3, wherein
the plurality of types of bloodstream information includes the velocity, dispersion, and power data; and
the coordinate conversion part is configured to simultaneously perform coordinate conversions and interpolations of the velocity, dispersion, and power data, by making them correspond to the three parallel processing circuits.

6. An ultrasonic imaging apparatus, comprising:
a transmitter/receiver configured to scan a subject body with ultrasonic waves via an ultrasonic probe, and to obtain first ultrasonic data including ultrasonic data in a first coordinate system that is along a scanning line;
an image generator including a processor configured to perform parallel processing;
a B-mode processor configured to generate the B-mode data as a portion of the first ultrasonic data and to cause the image generator to generate converted B-mode data;
a bloodstream information processor configured to generate velocity, dispersion, and power data as an additional portion of the first ultrasonic data and to cause the image generator to generate converted velocity, dispersion, and power data;
an image display controller configured to synthesize the converted B-mode data with the converted velocity, dispersion, and power data, and to determine a combination of the B-mode data and the converted velocity, dispersion, and power data to be displayed at each point, based on image conditions and the threshold information; and
a coordinate conversion part configured to perform an arithmetical operation using the processor, and to convert the first ultrasonic data from the first coordinate system into a second coordinate system for image display,
wherein the image display controller includes exactly four parallel processing circuits, including three parallel processing circuits and an alpha circuit, wherein, in one mode, the three parallel processing circuits are configured to process color and the alpha circuit is configured to process opacity, and in another mode, the alpha circuit stores the threshold information and is configured to perform the synthesizing process to synthesize the B-mode data and the velocity, dispersion, and power data, and the three parallel processing circuits are configured to generate B-mode images and generate Doppler images from the velocity, dispersion, and power data in parallel with the synthesizing process performed by the alpha circuit,
the coordinate conversion part is further configured to perform an interpolation arithmetical operation of interpolating one point in the second coordinate system by using the processor, based on a plurality of points in the first coordinate system, and
in performing the interpolation arithmetical operation, upon reception of an input of a kernel size that is a size for filtering, the kernel size being a higher order than 2×2, low-order 2×2 bi-linear interpolation is performed by the processor to determine first interpolation values, and a second interpolation value is found by executing a program of the processor that implements higher-order interpolation than 2×2, based on the determined first interpolation values and a predetermined interpolation function.

7. The ultrasonic imaging apparatus according to claim 6, wherein:
the processor is configured to perform graphic drawing instead of a CPU.

8. A method for displaying diagnostic images, comprising:
scanning a subject body with ultrasonic waves via an ultrasonic probe, and obtaining first ultrasonic data including ultrasonic data in a first coordinate system that is along a scanning line;
performing an arithmetical operation by a graphic processing unit (GPU), and performing coordinate conversion of the first ultrasonic data from the first coordinate system to a second coordinate system for image display;
generating B-mode data as a portion of the first ultrasonic data, and generating converted B-mode data;
generating velocity, dispersion, and power data as an additional portion of the first ultrasonic data, and generating converted velocity, dispersion, and power data; and
synthesizing the converted B-mode data with the converted velocity, dispersion, and power data, and determining a combination of the B-mode data and the converted velocity, dispersion, and power data to be displayed at each point, based on image conditions and threshold information, wherein
the GPU includes an image display controller including exactly four parallel processing circuits including three parallel processing circuits and an alpha circuit, wherein, in one mode, the three parallel processing circuits process color and the alpha circuit processes opacity, and in another mode, the alpha circuit stores the threshold information and is configured to perform the synthesizing step to synthesize the B-mode data and the velocity, dispersion, and power data, and the three parallel processing circuits are configured to generate B-mode images and generate Doppler images from the velocity, dispersion, and power data in parallel with the synthesizing step performed by the alpha circuit,
the step of performing the coordinate conversion comprises performing an interpolation arithmetical operation to interpolate, using the GPU, one point in the second coordinate system, based on a plurality of points in the first coordinate system, and the step of performing the interpolation arithmetical operation comprises, upon reception of an input of a kernel size that is a size for filtering, the kernel size being a higher order than 2×2, performing low-order 2×2 bi-linear interpolation by a hardware circuit of the GPU to determine first interpolation values, and finding a second interpolation value by executing a program loaded by a programmable processor of the GPU that implements higher-order interpolation than 2×2, based on the first interpolation values and a predetermined interpolation function.

9. The method for displaying diagnostic images according to claim 8, wherein:

the coordinate conversion comprises obtaining geometric conversion data that makes the first coordinate system correspond to the second coordinate system, and performing geometric conversion by the GPU based on the geometric conversion data to perform the coordinate conversion.

10. The method for displaying diagnostic images according to claim 8, wherein the first ultrasonic data includes a plurality of types of bloodstream information, and the step of performing the coordinate conversion comprises simultaneously performing a plurality of coordinate conversions of the plurality of types of bloodstream information.

11. The method for displaying diagnostic images according to claim 8, wherein the step of performing the coordinate conversion comprises finding a complex number whose elements are the velocity, dispersion, and power data of a bloodstream included in the first ultrasonic data, calculating an interpolation value of the complex number, and thereafter, individually converting to the velocity, dispersion, and power data of the bloodstream based on the interpolation value to determine an interpolation value of the velocity, dispersion, and power data of the bloodstream.

12. The method for displaying diagnostic images according to claim 10, wherein the step of performing the coordinate conversion comprises simultaneously performing coordinate conversions and interpolations of the velocity, dispersion, and power data included in the plurality of bloodstream information, by making them correspond to the three parallel processing circuits.

* * * * *